United States Patent [19]
Hilborn et al.

[11] Patent Number: 5,936,124
[45] Date of Patent: Aug. 10, 1999

[54] FLUOXETINE PROCESS FROM BENZOYLPROPIONIC ACID

[75] Inventors: James Wallace Hilborn, Windsor; Alex Roger Jurgens, Falmouth, both of Canada; Chris Hugh Senanayake, Shrewsbury, Mass.

[73] Assignee: Sepacor Inc., Marlborough, Mass.

[21] Appl. No.: 09/102,418

[22] Filed: Jun. 22, 1998

[51] Int. Cl.[6] .................................................. C07C 213/00
[52] U.S. Cl. .......................... 564/347; 564/356; 549/322; 549/326; 544/88
[58] Field of Search ..................................... 564/347, 342, 564/344, 355, 357, 356; 549/326, 322; 568/814; 544/88, 89; 548/240

[56] References Cited

U.S. PATENT DOCUMENTS

| | | | |
|---|---|---|---|
| 2,701,246 | 2/1955 | Dreschel . | |
| 4,018,895 | 4/1977 | Molloy et al. | 424/330 |
| 4,194,009 | 3/1980 | Molloy et al. | 424/330 |
| 4,314,081 | 2/1982 | Molloy et al. | 564/347 |
| 4,626,549 | 12/1986 | Molloy et al. | 514/651 |
| 4,868,344 | 9/1989 | Brown | 568/812 |
| 5,104,899 | 4/1992 | Young et al. | 514/646 |
| 5,420,306 | 5/1995 | Noyori | 549/326 |
| 5,589,511 | 12/1996 | Young et al. | 514/646 |
| 5,648,396 | 7/1997 | Young et al. | 514/651 |
| 5,760,243 | 6/1998 | Theriot | 548/240 |
| 5,847,214 | 12/1998 | Arosio | 564/347 |

FOREIGN PATENT DOCUMENTS

| | | |
|---|---|---|
| 0336753 | 4/1989 | European Pat. Off. . |
| 0369685 | 5/1990 | European Pat. Off. . |
| 0457559 | 5/1991 | European Pat. Off. . |
| 0529842 | 3/1993 | European Pat. Off. . |
| 0617006 | 4/1994 | European Pat. Off. . |
| 0380924 | 6/1994 | European Pat. Off. . |
| 2060618 | 5/1981 | United Kingdom . |
| WO94/00416 | 6/1994 | WIPO . |

OTHER PUBLICATIONS

J Chem Soc by Barton , "Novel synthesis of Lactones" pp. 181–190, 1965.

J Org Chem vol. 33 by Sullivan "The preparation of 6–Aryltetrahydro–1,3–oxazin–2–ones " pp. 2134–2136, 1968.

J Org Chem vol. 26 by Smith " The cyclization of N–Akenylthionamides to thiazolines and dihydrothiazines" pp. 1132–1136, 1961.

CA:110:7786 abs Tetrahedron letts, 29(12), pp. 1457–1460, 1988.

March Advanced Organic Chemistry p. 320–21, 1968.

Kumar et al. "A New Chemoenzymatic Enantioselective Synthesis of R–(–)–Tomoxetine, (R)–. . . " *Tetrahedron Letters* 32, 1901–1904 (1991).

Ager and Laneman "Reductions of 1,3–dicarbonyl systems with ruthenium–biarylbisphosphine . . . " *Tetrahedron: Asymmetry* 8, 3327–3355 (1997).

Quirós et al. "Enantioselective reduction of β–keto amides by the fungus *Mortierella isabellina*" *Tetrahedron: Asymmetry* 8, 3035–3038 (1997).

Mitchell and Koenig "Synthesis of R–and S–Fluoxetine, Norfluoxetine and Related . . . " *Synthetic Comm.* 25(8), 1231–1238 (1995).

Senanayake et al. "Nature of N–Bromosuccinimide in Basic Media: The True Oxidizing . . . " *J. Amn. Chem. Soc.* 116, 7947–7948 (1994).

*Primary Examiner*—Paul J. Killos
*Assistant Examiner*—Jean F Vollano
*Attorney, Agent, or Firm*—Heslin & Rothenberg, P.C.

[57] ABSTRACT

A synthesis of fluoxetine is disclosed. The process begins with a lower alkyl ester of 3-benzoylpropionic acid, which is reduced in the presence of a chiral ligand to produce the corresponding γ-hydroxy ester, and the ester is cleaved. The free acid is then condensed with the alcohol to form a γ-lactone, which is treated with ammonia to provide the γ-hydroxy amide. The amide undergoes a Hoffman rearrangement to provide a 2-oxo-1,3 oxazine, which is reduced to 3-(methylamino)-1-phenyl-1-propanol. The alcohol is deprotonated and reacted with a 4-chloro- or 4-fluoro benzotrifluoride to provide fluoxetine free base.

16 Claims, No Drawings

FLUOXETINE PROCESS FROM BENZOYLPROPIONIC ACID

FIELD OF THE INVENTION

This invention relates to a process for preparing fluoxetine, a commercially available pharmaceutical.

BACKGROUND OF THE INVENTION

Fluoxetine is a selective serotonin uptake inhibitor presently available for the treatment of depression under the trade name Prozac™. Its chemical name is given as N-methyl-3-phenyl-3-[(α,α,α-trifluoro-p-tolyl)oxy] propylamine in much of the literature; its name for indexing in Chemical Abstracts is (+/−)-N-methyl-γ-[4-(trifluoromethyl)phenoxy]benzenepropanamine. Fluoxetine is currently available for therapy as a racemic mixture only. Early reports indicated that there was no advantage to the use of the either pure enantiomer [Robertson et al. *J. Med. Chem.* 31, 1412–1417 (1988)] of fluoxetine. However, subsequent publications have suggested advantages to the use of the pure S(+) isomer [U.S. Pat. Nos. 5,104,899 and 5,589,511] and the pure R(−) isomer [U.S. Pat. No. 5,648,396]. Thus, processes for the commercial preparation of racemic fluoxetine and of each of its enantiomers are of considerable value. Throughout this application, various references are referred to within parentheses or square brackets. The disclosures of these publications in their entireties are hereby incorporated by reference into this application.

Numerous processes are known in the literature. The original U.S. patents to fluoxetine [U.S. Pat. Nos. 4,314,081 and 4,194,009] describe syntheses beginning from 3-dimethylaminopropiophenone, which is reduced with diborane, chlorinated with thionyl chloride, condensed with 4-trifluoromethylphenol, and demethylated with cyanogen bromide and potassium hydroxide in ethylene glycol. This process was somewhat improved by Robertson et al. [*J. Labeled Compound Radiopharm.* 24, 1397–1404 (1987)] by condensing the alcohol with 4-chlorobenzotrifluoride and by replacing cyanogen bromide with phenylchloroformate.

European application 519842 discloses an improved process in which 3-dimethylamino-1-phenyl-1-propanol is reacted with an alkyl chloroformate and hydrolyzed to provide 3-methylamino-1-phenyl-1-propanol, which is then condensed with 4-chloro- or 4-fluorobenzotrifluoride. European application 457559 describes a chiral synthesis of the 3-dimethylamino-1-phenyl-1-propanol that is used as a starting material in the foregoing European application. The chiral synthesis is accomplished by reduction of the corresponding ketone with lithium aluminum hydride using (2R,3S)-(−)4-dimethylamino-1,2,-diphenyl-3-methyl-2-butanol as a chiral ligand. A similar chiral reduction has been described by Sakuraba et al. [*Syn. Lett.* 1991, 689–690] using a different chiral reducing agent. Another approach, described in European patent 380924, proceeds by reduction of ethylbenzoylacetate and subsequent aminolysis of the ethyl ester with methylamine. The reduction of ethylbenzoylacetate can also be accomplished in an enantioselective manner using baker's yeast [Kumar et al. *Indian J. Chem.* 31B, 803–809 (1992)]. A ruthenium catalyst having a chiral ligand has been employed in a similar catalytic reduction by Ager and Laneman [*Tet. Asymmetry* 30, 3327–3355 (1997)].

Numerous other methods have been described for preparing single enantiomers of fluoxetine. These include chiral epoxidation of styrene followed by ring opening with acetone cyanohydrin [Mitchell and Koenig *Synthetic Comm.* 25, 1231–1238 (1995)]; asymmetric borane reduction of β-chloropropiophenone [Corey et al. *Tet. Lett.* 30, 5027 (1989)]; and asymmetric epoxidation/reduction [Gao et al. *J. Org. Chem.* 53, 4081–4085 (1988)].

SUMMARY OF THE INVENTION

This invention relates to an improved process for the preparation of fluoxetine, and, in particular, individual fluoxetine enantiomers.

In one aspect, the invention relates to a process for preparing the fluoxetine precursor, 3-(methylamino)-1-phenylpropanol 6. The process, which is shown in Scheme I, comprises the steps of:

(a) reacting 5-phenyltetrahydrofuran-2-one 2 with an excess of ammonia to provide 4-hydroxybenzenebutanamide 3;

(b) reacting the 4-hydroxybenzenebutanamide with an oxidant to provide 6-phenyltetrahydrooxazin-2-one 4; and (c) reducing the 6-phenyltetrahydrooxazin-2-one to provide 3-(methylamino)-1-phenylpropanol 6.

In a modification of step (c) of the foregoing process (also shown in Scheme I), the 6-phenyltetrahydrooxazin-2-one 4 may be reacted with a strong base followed by a methylating agent to provide 3-methyl-6-phenyltetrahydrooxazin-2-one 5, which may be hydrolyzed to provide 3-(methylamino)-1-phenylpropanol 6.

The starting material 2 for the above process steps may be obtained by (i) reducing a lower alkyl ester of 3-benzoylpropionic acid 1 with borane to provide a lower alkyl ester of 4-phenyl-4-hydroxybutanoic acid. If the reduction is carried out in the presence of a chiral ligand, the product is enriched in one enantiomer (not shown);

(ii) hydrolyzing the ester to provide 4-hydroxy-4-phenylbutanoic acid (not shown); and (iii) treating the 4-hydroxy-4-phenylbutanoic acid with a catalytic amount of an acid to form the lactone 2.

3-(Methylamino)-1-phenylpropanol 6 is an intermediate in the synthesis of fluoxetine. It may be converted to the immediate precursor of the drug (i.e. the free base) by reacting with a strong base followed by 4-chlorobenzotrifluoride or 4-fluorobenzotrifluoride to provide N-methyl-3-phenyl-3-[(α,α,α-trifluoro-p-tolyl)oxy] propylamine 7, also known as fluoxetine free base. The free base may be converted to a salt, such as fluoxetine hydrochloride 8, by treatment of a solution of the free base with a salt-forming acid, such as anhydrous HCl in ether. The process is particularly useful for the preparation of single enantiomers of fluoxetine, providing S-fluoxetine in >98% ee and 36% overall chemical yield from methyl 3-benzoylpropionate.

SCHEME I

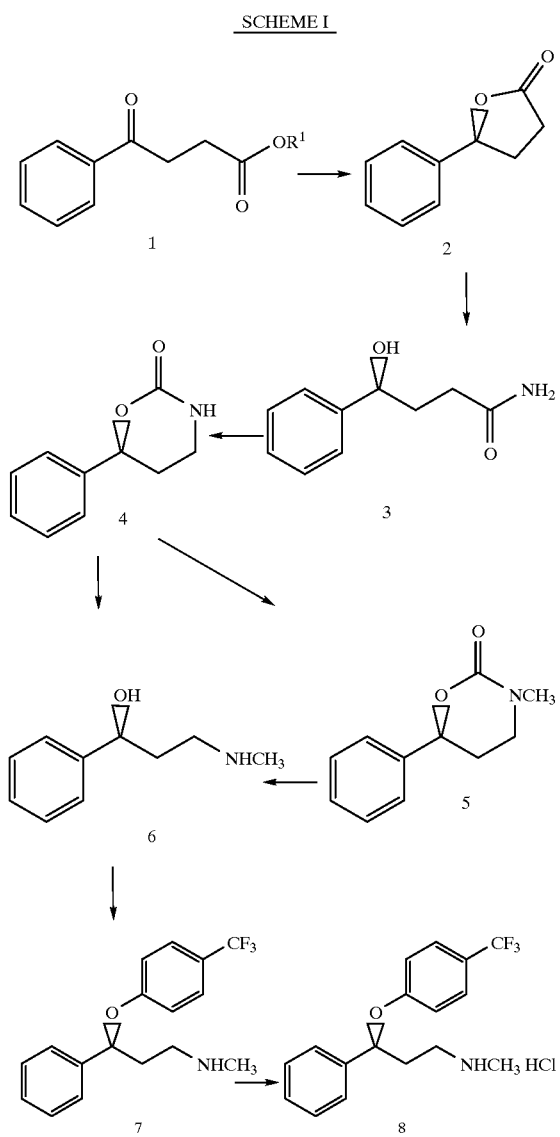

DETAILED DESCRIPTION OF THE INVENTION

The overall synthesis described in Scheme 1 can be further characterized as follows: The process begins with a lower alkyl ester of 3-benzoylpropionic acid 1. In preferred embodiments, lower alkyl is methyl, ethyl or t-butyl. The benzoylpropionate is reduced in the presence of a chiral ligand to produce the corresponding γ-hydroxy ester. A preferred reagent is β-chlorodiisopino camphenyl borane, but other combinations of borane and a chiral ligand are possible, such as the borane aminoindanol reagents described by Gao et al. [U.S. Pat. No. 5,495,054]. Reduction can also be carried out using other metal hydride reducing agents and chiral ligands, as well as by asymmetric hydrogenation and asymmetric transfer hydrogenation. When reduction of the ketone to the alcohol is complete, the ester is cleaved. If the ester is a methyl or ethyl ester, it can be conveniently cleaved by aqueous alkali metal hydroxides; when the ester is a t-butyl ester, it may be conveniently cleaved by treatment with anhydrous acid, such as HCl in ether. The free acid is then condensed intramolecularly with the alcohol to form a γ-lactone. This is accomplished by any of the methods well known in the art for forming butyrolactones; the use of acids such as pyridinium p-toluenesulfonate is particularly convenient.

The γ-butyrolactone 2 is treated with an excess of ammonia in a polar solvent such as methanol, to provide the γ-hydroxy amide 3.

In an alternative route to the γ-hydroxy amide 3,3-benzoylpropionamide may be reduced with the same reagents described above for the lower alkyl ester of 3-benzoylpropionic acid 1. Alternatively, the asymmetric reduction of 3-benzoylpropionamide may be accomplished enzymically according to the method of Quiros et al. [*Tetrahedron Asymmetry* 8, 3035–3038 (1997)].

The amide 3 is treated with any of the reagents known for carrying out the Hoffman rearrangement. Typical reagents that have been found useful as oxidants in the Hoffman rearrangement include iodine (III) reagents, such as iodobenzene diacetate and iodobenzene-bis-trifluoroacetate; lead tetraacetate; ammonium tribromide complexes, such as benzyltrimethylammonium tribromide and pyridinium hydrobromide perbromide; alkaline bromine solutions; N-bromosuccinimide and N-bromosuccinimide in combination with mercuric and argentic salts. A good review is provided by Senanayake et al. [*J. Am. Chem. Soc.* 116, 7947–7948 (1994)]. In an aprotic solvent, such as acetonitrile, the intermediate isocyanate is captured by the γ-hydroxyl, and a 2-oxo-1,3-oxazine (also called a cyclic carbamate or cyclic urethane) 4 is formed.

Two options are available for the conversion of the oxazine to 3-(methylamino)-1-phenyl-1-propanol 6. The direct route involves the reduction and cleavage of the carbamate carbon using a hydride reagent, such as lithium aluminum hydride, or a borane reagent, such as borane dimethyl sulfide in an inert solvent, usually of the ether class, such as THF. If the process of the invention is used to prepare a single enantiomer product, it is preferred to avoid highly acidic conditions during workup of the reaction. Thus, for example, excess borane would be destroyed by reacting with a base, such as aqueous sodium hydroxide, as opposed to an acid, such as aqueous hydrochloric acid. Alternatively, the oxazine may be methylated on nitrogen by means known in the art for methylating the nitrogen of carbamates. One useful approach is hydrogen abstraction with a strong base, such as sodium hydride or potassium t-butoxide followed by methylation with a methylating reagent, such as methyl iodide or methyl sulfate. The resulting N-methyloxazin-2-one 5 may be hydrolyzed to 3-(methylamino)-1-phenyl-1-propanol 6 or, in a variant described below, the N-methyl carbamate may be taken directly to fluoxetine free base 7 by sulfuration and ring opening with trifluoromethyl phenoxide. The hydrolysis of 5 to 6 is most readily accomplished by alkali metal hydroxide in an aqueous solution. The aqueous solution will commonly include an additional polar solvent such as ethanol or methanol to aid in solubility of the starting material.

The conversion of 3-(methylamino)-1-phenylpropanol 6 to fluoxetine free base 7 may be accomplished by one of several means. The alcohol 6 may be deprotonated with a strong base such as sodium hydride in anhydrous solvent such as DMSO and the resulting sodium alcoholate reacted with a 4-chloro- or 4-fluoro-benzotrifluoride. Alternatively, the alcohol 6 may be deprotonated with sodium hydroxide in DMSO and arylated in similar fashion. A third alternative is the reaction of the alcohol 6 with 4-trifluoromethyl phenol under Mitsunobu conditions with trivalent phosphorous and diethyl azodicarboxylate. In this case, however, inversion will occur, and the resulting fluoxetine free base 7 will be of the opposite configuration from 6 at the alcohol carbon. Finally, the fluoxetine free base 7 is converted to fluoxetine hydrochloride by treatment with anhydrous HCl and recrystallization. A fourth method of condensation comprises reacting the N-methyl alcohol 6 with sulfuryl chloride or with thionyl chloride and then $RuCl_6/NaIO_4$ to provide a 2,2-dioxo-1,2,3-oxothiazine, which may be ring opened with 4-trifluoromethyl phenoxide anion.

As mentioned above, an alternative pathway can be provided from the N-methyl carbamate 5 to fluoxetine free base 7. According to this alternate route, the N-methyl carbamate is treated with a sulfurating reagent such as Lawesson's reagent, [2,4-bis(4-methoxyphenyl)-1,3-dithia-2,4-diphosphetane-2,4-disulfide] to provide the corresponding n-methyl thiocarbamate. The thiocarbamate may be ring opened with 4-trifluoromethyl phenoxide anion.

The graphic representations of racemic, ambiscalemic and scalemic or enantiomerically pure compounds used herein are taken from Maehr *J. Chem. Ed.* 62, 114–120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, the formula 7 means either of the pure enantiomers of that pair:

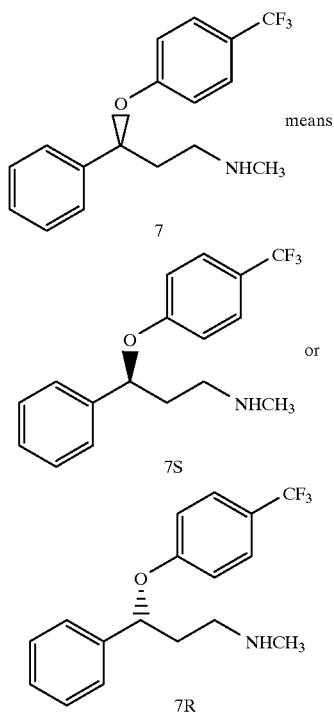

The term "enantiomeric excess" is well known in the art and is defined for a resolution of ab→a +b as $$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee.; in other words, a 90% e.e. reflects the presence of 95% of one enantiomer and 5% of the other in the material in question.

Alkyl is intended to include linear, branched, or cyclic hydrocarbon structures and combinations thereof. Lower alkyl refers to alkyl groups of from 1 to 4 carbon atoms. Examples of lower alkyl groups include methyl, ethyl, propyl, isopropyl, butyl, s-and t-butyl and the like.

Abbreviations and Definitions

The following abbreviations and terms have the indicated meanings throughout:

Ac=acetyl
BNB=4-bromomethyl-3-nitrobenzoic acid
Boc=t-butyloxy carbonyl
Bu=butyl
c-=cyclo
DBU=diazabicyclo[5.4.0]undec-7-ene
DCM=dichloromethane=methylene chloride=$CH_2Cl_2$
DEAD=diethyl azodicarboxylate
DIC=diisopropylcarbodiimide
DIEA=N,N-diisopropylethyl amine
DMAP=4-N,N-dimethylaminopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
Me=methyl
mesyl=methanesulfonyl
MTBE=methyl t-butyl ether
NMO=N-methylmorpholine oxide
PEG=polyethylene glycol
Ph=phenyl
PhOH=phenol
Pfp=pentafluorophenol
PPTS=pyridinium p-toluenesulfonate
PyBroP=bromo-tris-pyrrolidino-phosphonium hexafluorophosphate
rt=room temperature
sat'd=saturated
s-=secondary
t-=tertiary
TBDMS=t-butyldimethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl

EXAMPLES t-Butyl 3-Benzoylpropionate (1; $R^1$=tBu): To a 500 mL round bottom flask was added 10.40 g (0.0426 mol) of 2,4,6-trichlorobenzoyl chloride. To this was added 300 mL of THF followed by 7.65 g (0.0429 mol) of 3-benzoylpropionic acid (I). Once the 3-benzoylpropionic acid had dissolved, then 6.1 mL (0.0830 mol) of triethylamine was added. The solution was stirred for 6 hours, after which the THF solution was filtered to remove the triethylamine hydrochloride. The filtrate was rotoevaporated to yield a light beige solid. To this solid was added 200 mL of benzene followed by 6.0 mL (0.104 mol) of 2-methyl-2-propanol and the mixture was stirred with heating to dissolve all of the solid. After complete dissolution, 5.40 g (0.0442 mol) of DMAP was added to the solution. The solution immediately turned dark red and was stirred at room temperature for 36 hours. The solution was washed with 10% aqueous HCl solution, followed by 2×5% aq. NaOH solution and finally with water. The organic layer was then dried (MgSO$_4$), filtered and concentrated. The resultant oil was purified twice by column chromatography (silica gel, Eluent: 20% ethyl acetate: hexanes) and the resultant oil obtained was distilled under reduced pressure to yield 6.45 g (64%) of t-butyl 3-benzoylpropionate as a colorless oil.

lit bp 129–130° C. at 1.5 mm Hg.; $^1$HNMR ppm ($\delta$), CDCL$_3$ 7.98 (d, 2H), 7.54 (m, 1H), 7.46 (m, 2H), 3.26 (t, 2H), 2.68 (t, 2H), 1.45 (s, 9H). $^{13}$CNMR ppm ($\delta$), CDCl$_3$, 198.3 (C=O), 172.1 (CO$_2$), 136.7 (q), 133.0, 128.6, 128.0, 80.6 (C(CH$_3$)$_3$), 33.5, 29.4, 28.0 (CH$_3$).

Methyl 3-Benzoylpropionate (1; R$^1$=Me): To a 1.0 L round bottom flask was added 49.25 g (0.276 mol) of 3-benzoylpropionic acid. To this was added 700 mL of ACS methanol and the solution stirred until all of the acid had dissolved. To this solution was added approximately 2.0 mL of conc. H$_2$SO$_4$ and the reaction refluxed for 2.5 hours. The reaction can be monitored by HPLC. After the reaction was determined to be complete, the methanol was removed on the rotoevaporator and to the residual oil was added ethyl acetate (~500 mL). To the ethyl acetate layer was then added 150 mL of a saturated sodium carbonate solution. The layers were extracted and allowed to separate. The organic layer was then dried (MgSO$_4$), filtered and concentrated to yield methyl 3-benzoylpropionate (1) as a light yellow oil. Yield 53.30 g; yield 100%; >97% cp.

Lt bp 172–174° C. at 10 mm Hg.; $^1$H NMR ppm ($\delta$), CDCl$_3$, 7.98 (dd, 2H), 7.54 (m, 1H), 7.45(m, 2H), 3.70 (s, 3H, OCH$_3$), 3.32 (t, 2H), 2.76 (t, 2H). $^{13}$C NMR ppm ($\delta$), CDCl$_3$ 198.0 (C=O), 173.3 (CO$_2$), 136.5 (q), 133.2, 128.6, 128.0, 51.7 (OCH$_3$), 33.3, 28.0. IR oil cm$^{-1}$ 2952, 1737, 1687, 1596, 1449, 1358, 1221, 1168, 1001, 750, 691.

The Preparation of the Chiral Lactone (2): To a 500 mL round bottom flask was added 30.5 g (0.0951 mol) of (-)-DIP-Cl [(-)-B-chlorodiisopinocamphenylborane]. To this was added 30 mL of dry THF at room temperature over 15 minutes. Once dissolved, the solution was cooled to –25° C. While maintaining the temperature between –20 and –25° C., to this solution was added dropwise 10.80 g (0.0561 mol) of methyl 3-benzoylpropionate (1,R$^1$=Me) in 15 mL of dry THF over 30 minutes. Note: During the addition of the ketoester the reaction mixture turned milky white in color and after all of the material was added the reaction mixture turned clear. The reaction was maintained between –10 and –20° C. for 8 hours and the reaction progress was monitored by HPLC. After 8 hours the reaction mixture was allowed to warm to –5° C. and finally to 0° C. in order to increase the rate of reaction. The reaction was stopped after all of the starting material was gone. To the reaction mixture was added slowly 26 mL of water (1.44 mol) over 10 minutes keeping the temperature below 10° C. Methanol was then added (66 mL, 1.63 mol) followed by 76 mL of a 5 M aqueous NaOH solution keeping the temperature below 10° C. The mixture was stirred for 2 hours and checked periodically by HPLC. After 2 hours the reaction was shown to be complete. The light yellow solution was poured into 500 mL of MTBE and 200 mL of sat. NaHCO$_3$ solution. After the extraction the layers were separated and the aqueous layer re-extracted with 200 mL of MTBE. The layers were again separated and the aqueous layer acidified to pH=2 with 6 M aq. HCl. The aqueous layer was saturated with NaCl and then extracted 3 times with 300 mL of ethyl acetate. The ethyl acetate layer was rotoevaporated and the residue taken up in toluene (1000 mL). To the toluene was added 1.5 g (0.006 mol) of PPTS and the solution was heated to reflux for 2 hours until the lactonization was complete. The solution was cooled to room temperature and washed twice with a saturated aq. NaHCO$_3$ solution. The toluene layer was rotoevaporated to yield 8.36 g (92%) of the lactone (2). The chemical purity was 97.3% and the optical purity was 98.75 ip (97.5%, e.e.).

The Preparation of (S)-4-hydroxy-4-phenylbutanamide (3): To a 500 mL round bottom flask was added 5.43 g (0.0334 mol) of the chiral lactone (2). To this oil was added 300 mL of a 2M solution of ammonia in methanol (0.600 mol) and the solution was stirred at 40° C. for 8 hours. At this point there was still 15% (by area %) of the lactone remaining. The solution was stirred for an additional 22 hours at 40° C. and the reaction was complete. The ammonia in methanol was removed on the rotoevaporator and to the residual oil was added approximately 30 mL of ethyl acetate. The ethyl acetate was allowed to evaporate slowly and yielded a white solid (5.44 g, 92%. mp=87–88° C.).

$^1$HNMR ppm ($\delta$), CDCl$_3$ 7.35–7.24 (m, 5H), 5.79 (s, 2H, NH$_2$), 4.77 (dd, 1H,CH—O), 3.66 (s, 1H, OH), 2.40–2.21 (m, 2H). $^{13}$C NMR ppm ($\delta$), CDCl$_3$ 176.4 (C=O), 144.6 (q), 128.7, 127.7, 126.0, 73.7 (C-0), 34.3, 32.3. MS (70 eV) 180 (M+1), 179 (M$^+$)

The Preparation of the Cyclic Carbamate (4): To a 250 mL round bottom flask was added 3.44 g (0.0192 mol) of the chiral alcohol amide (3). The material was dissolved in 100 mL of acetonitrile and then 7.61 g (0.0236 mol) of iodobenzene diacetate was added. The solution was stirred at 40° C. for 4 hours monitoring the reaction by HPLC. After the reaction was complete, the acetonitrile was removed on the rotoevaporator and the oil taken up in ethyl acetate. The oil was purified by column chromatography using silica gel and eluting with ethyl acetate. The fractions containing the carbamate were combined, concentrated and recrystallized from ethyl acetate to give 3.16 g of the product (93% yield). Chemical purity=100%, Isomeric Purity=99.7%, mp=191–192° C.

$^1$H NMR ppm ($\delta$), CDCl$_3$ 7.37–7.29 (m, 5H), 6.65 (s, 1H, NH), 5.34 (dd, 1H,CH—O), 3.48–3.36(m,2H), 2.19–2.05 (m, 2H). $^{13}$C NMR ppm ($\delta$) CDCl$_3$ 155.3 (C=O), 139.3 (q), 128.8, 128.6, 125.9, 78.8 (C—O), 39.0, 28.9. IR KBr cm$^{-1}$ 3303, 1690, 1664, 1482, 1457, 1300, 1137, 1051, 767, 756, 697. MS (70 eV) 178 (M+1), 177.1 (M$^+$)

The Preparation of (S)-3-(Methylamino)-1-phenyl-1-propanol (6): To a 250 mL round bottom flask was added 1.62 g (0.00914 mol) of the cyclic carbamate (4). To this was added 100 mL of THF followed by 4.6 mL of BH$_3$ DMS (0.046 mol) and the mixture was heated to reflux for 4 hours. The reaction mixture was allowed to cool to room temperature and conc. HCl was added very slowly. After stirring for one hour to destroy all of the borane, the solvent was removed by rotoevaporation to yield an oil. The oil was taken up in a solution of 2M aq. HCl. The aqueous layer was washed with chloroform, neutralized with solid sodium hydroxide and the aqueous layer extracted with ethyl acetate (3×200 mL). The ethyl acetate layer was dried (MgSO$_4$), filtered and rotoevaporated to yield an oil. The oil was taken up 3 times in methanol and concentrated under reduced pressure to remove any excess B(OCH$_3$)$_3$. The yield of the chiral amino alcohol (6) was 1.18 g (78%).

$^1$H NMR ppm (δ), CDCl$_3$ 7.38–7.22 (m, 5H), 4.90 (dd, 1H,CH—O), 4.15 (s, 2H, OH&NH), 2.88–2.82 (m,2H), 2.42 (s, 3H, NCH$_3$), 1.88–1,75 (m,2H). $^{13}$C NMR ppm (δ), CDCl$_3$ 145.0, 128.2, 127.0, 125.6, 75.2, 50.2, 26.8, 35.9.

Preparation of the N-methyl cyclic carbamate (5): To a 250 mL round bottom flask was added 0.54 g (0.0030 mol) of the cyclic carbamate and 20 mL of DMF, and the mixture was stirred until dissolved. To this was then added 0.11 g (0.0046 mol) of dry NaH. The mixture was stirred for 20 min at room temperature, 0.70 mL of methyl iodide (0.0111 mol) was added and the mixture was stirred at room temperature for 2 hours. The DMF solution was poured into 100 mL of brine and extracted three times with EtOAc. The EtOAc layers were combined, washed three times with brine to remove any residual DMF. The EtOAc layer was dried (MgSO$_4$), filtered and rotoevaporated to yield 0.52 g of a white solid. The crude material was purified by recrystallization from ethyl acetate to yield 0.42 g (72%) of the product. Chemical purity=>97%, mp=105–107° C.

$^1$H NMR ppm (δ), CDCl$_3$ 7.38–7.31 (m, 5H), 5.28 (dd, 1H, CH—O), 3.53–3.42 (m, 1H), 3.27–3.20 (m, 1H), 3.03 (s, 1H, NCH$_3$), 2.25–2.12 (m, 2H). $^{13}$C NMR ppm (δ), CDCl$_3$, 153.8, 139.0, 128.6, 128.3, 125.6, 78.2, 46.3, 36.6, 29.6. IR oil cm$^-$2935, 1678, 1493, 1438, 1329, 1254, 1144, 1069, 762, 705.

Preparation of (S)-2-(Methylamino)-1-phenyl-1-propanol (6) by hydrolysis of the N-methyl cyclic carbamate (5): To a 125 mL round bottom flask was added 0.54 g (0.028 mol) of the N-methyl cyclic carbamate. To this was added 20 mL of ethanol followed by a solution of 1.36 g of NaOH (0.034 mol) in 5 mL of water. This solution was refluxed for 2 hours and then allowed to cool to room temperature. The mixture was filtered to remove a white precipitate and the filtrate concentrated on the rotoevaporator to obtain an oil. The oil was taken up in ethyl acetate and washed three times with brine. The organic layer was then dried, filtered and rotoevaporated to yield 0.48 g (104%) of a light yellow oil.

The Preparation of Fluoxetine Free Base (7): To a 3.0 L round bottom flask was added 24.5 (0.148 mol) of the aminoalcohol (6) and this was dissolved in 215 mL of DMSO. To this solution was then added 5.72 g (0.238 mol) of sodium hydride (washed with hexanes). The solution was heated to 60° C. for 1 hour. To this dark orange solution was added 50 mL of 4-chlorobenzotrifluoride (0.374 mol). The reaction mixture was heated to 115° C. for 6 hours. The reaction was allowed to cool to room temperature and then 1.0 L of water was added to quench the reaction. The reaction mixture was extracted with ethyl ether (2×500 mL), followed by two extractions using toluene (2×500 mL). The organic layers were combined and washed twice with brine. The aqueous layer was separated and the organic layer dried, filtered and rotoevaporated to yield 60.3 g of crude material. This crude material was purified by column chromatography (silica gel) using 5% methanol:methylene chloride as the eluent. Yield of pure fluoxetine free base (7) was 25.6 g (56%). Chemical purity=96.9%

$_1$H NMR ppm (δ), CDCl$_3$ 7.57 (d,2H), 7.44–7.24 (m, 5H), 6.91 (d, 2H), 5.33 (dd, 1H), 2.75 (t, 2H), 2.42 (3H, NCH$_3$), 2.20 (m, 1H), 1.90 (s, 1H). $^{13}$C NMR ppm (δ), CDCl$_3$ 160.6, 141.0, 128.8, 127.8, 126.7, 125.8, 122.7, 115.8, 78.7, 48.2, 38.7, 36.4.

The Preparation of Fluoxetine Hydrochloride (8): To a 3.0 L round bottom flask was added 25.5 g (0.0824 mol) of fluoxetine free base. To this was added 850 mL of diethyl ether and the amine was dissolved. To this solution was added 150 mL of an ethereal hydrochloric acid solution (0.069 mol HCl/100 mL). The reaction was stirred for 30 minutes and then the ether was rotoevaporated to dryness. The solid was taken up in a minimum of ethyl acetate and hexane was added until crystals started forming. The white solid was placed in the refrigerator for 14 hours at ~5° C. The solution was filtered and dried to give 25.75 g of fluoxetine hydrochloride (90%).

$^1$H NMR ppm (δ), CDCl$_3$ 7.43–7.23 (m,9H), 5.71 (s,2H, NH$_2$),5.38 (dd, 1H, CH—O), 290 (m, 2H), 250 (s, 3H, NCH$_3$), 2.35–2.18 (m, 2H). $^{13}$C NMR ppm (δ), CDCl$_3$ 160.2, 140.3, 128.9, 128.1, 126.18, 126.7, 125.8, 123.0, 115.8, 78.0, 47.3, 37.0, 35.0.

We claim:

1. A process for preparing 3-(methylamino)-1-phenylpropanol comprising the steps of:
   (a) reacting 5-phenyltetrahydrofuran-2-one with an excess of ammonia to provide 4-hydroxybenzenebutanamide;
   (b) reacting said 4-hydroxybenzenebutanamide with an oxidant to provide 6-phenyltetrahydrooxazin-2-one; and
   (c) reducing said 6-phenyltetrahydrooxazin-2-one to provide 3-(methylamino)-1-phenylpropanol.

2. A process according to claim 1 comprising the additional steps, before step (a), of:
   (i) reducing a lower alkyl ester of 3-benzoylpropionic acid with borane in the presence of a chiral ligand to provide a lower alkyl ester of 4-hydroxy-4-phenylbutanoic acid enriched in one enantiomer;
   (ii) hydrolyzing said lower alkyl ester to provide 4-hydroxy-4-phenylbutanoic acid; and
   (iii) treating said 4-hydroxy-4-phenylbutanoic acid with a catalytic amount of an acid to provide 5-phenyltetrahydrofuran-2-one enriched in one enantiomer.

3. A process according to claim 2 wherein said lower alkyl ester of 4-hydroxy-4-phenylbutanoic acid enriched in one enantiomer is methyl (S)-4-hydroxy-4-phenylbutanoate.

4. A process according to claim 1 or 2 wherein said 3-(methylamino)-1-phenylpropanol is (S)-3-(methylamino)-1-phenylpropanol.

5. A process according to claim 4 comprising the additional step, following all preceding steps, of reacting (S)-3-(methylamino)-1-phenylpropanol with a strong base followed by 4-chlorobenzotrifluoride to provide (S)-N-methyl-3-phenyl-3-[(α,α,α-trifluoro-p-tolyl)oxy]propylamine.

6. A process according to claim 1 or 2 wherein said 3-(methylamino)-1-phenylpropanol is (R)-3-(methylamino)-1-phenylpropanol.

7. A process according to claim 6 comprising the additional step, following all preceding steps, of reacting (R)-3-(methylamino)-1-phenylpropanol with a strong base followed by 4-chlorobenzotrifluoride to provide (R)-N-methyl-3-phenyl-3-[(α,α,α-trifluoro-p-tolyl)oxy]propylamine.

8. A process according to claim 1 wherein said oxidant in step (b) is chosen from iodine (III) reagents, alkaline bromine solutions, lead tetraacetate, ammonium tribromide complexes, alkaline solutions of N-bromosuccinimide and N-bromosuccinimide in combination with Ag (II) or Hg (II) salts.

9. A process according to claim 8 wherein said oxidant is iodobenzene diacetate.

10. A process according to claim 1 wherein said 6-phenyltetrahydrooxazin-2-one is reduced with borane or a metal hydride.

11. A process according to claim 10 wherein said metal hydride is lithium aluminum hydride.

12. A process according to claim 2 wherein said lower alkyl ester is a methyl ester and said ester is hydrolyzed with an alkali metal hydroxide in aqueous solution.

13. A process for preparing fluoxetine free base comprising the steps of:
(a) reacting 5-phenyltetrahydrofuran-2-one with an excess of ammonia to provide 4-hydroxybenzenebutanamide;
(b) reacting said 4-hydroxybenzenebutanamide with an oxidant to provide 6-phenyltetrahydrooxazin-2-one;
(c) reducing said 6-phenyltetrahydrooxazin-2-one to provide 3-(methylamino)-1-phenylpropanol; and
(d) reacting said 3-(methylamino)-1-phenylpropanol with a strong base followed by 4-chlorobenzotrifluoride to provide fluoxetine free base.

14. A process according to claim 13 comprising the additional steps, before step (a), of:

(i) reducing a lower alkyl ester of 3-benzoylpropionic acid with borane in the presence of a chiral ligand to provide a lower alkyl ester of 4-hydroxy-4-phenylbutanoic acid enriched in one enantiomer;

(ii) hydrolyzing said lower alkyl ester to provide 4-hydroxy-4-phenylbutanoic acid; and (iii) treating said 4-hydroxy-4-phenylbutanoic acid with a catalytic amount of an acid to provide 5-phenyltetrahydrofuran-2-one enriched in one enantiomer.

15. A process according to claim 14 wherein said 3-(methylamino)-1-phenylpropanol is (S)-3-(methylamino)-1-phenylpropanol whereby S-fluoxetine free base is produced.

16. A process according to claim 14 wherein said 3-(methylamino)-1-phenylpropanol is (R)-3-(methylamino)-1-phenylpropanol whereby R-fluoxetine free base is produced.

* * * * *

UNITED STATES PATENT AND TRADEMARK OFFICE
CERTIFICATE OF CORRECTION

PATENT NO. : 5,936,124
DATED : August 10, 1999
INVENTOR(S) : Hilborn et al.

It is certified that error appears in the above-identified patent and that said Letters Patent is hereby corrected as shown below:

ON THE TITLE PAGE:

ITEM [73] Assignee: Delete "Sepacor Inc." and replace with --Sepracor Inc.--.

Signed and Sealed this

Twenty-ninth Day of August, 2000

Attest:

Q. TODD DICKINSON

*Attesting Officer*     *Director of Patents and Trademarks*